(12) United States Patent
Bergman et al.

(10) Patent No.: US 6,673,819 B2
(45) Date of Patent: Jan. 6, 2004

(54) COMPOUNDS USEFUL AS ANTIBACTERIAL AGENTS

(75) Inventors: Rolf Bergman, Mölndal (SE); Arne Eek, Södertälje (SE); Lars-Inge Olsson, Södertälje (SE); Per Lindberg, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/028,399

(22) Filed: Dec. 20, 2001

(65) Prior Publication Data

US 2002/0111370 A1 Aug. 15, 2002

Related U.S. Application Data

(63) Continuation-in-part of application No. PCT/SE01/01421, filed on Jun. 20, 2001.

(30) Foreign Application Priority Data

Jun. 30, 2000 (SE) .............................................. 0002476

(51) Int. Cl.[7] .................. A61K 31/4439; C07D 401/12
(52) U.S. Cl. .................................... 514/338; 546/273.7
(58) Field of Search ......................... 546/273.7; 514/338

(56) References Cited

FOREIGN PATENT DOCUMENTS

| EP | 0005129 | 10/1979 |
|----|---------|---------|
| WO | 9009175 | 8/1990 |
| WO | 9321920 | 11/1993 |
| WO | 9944595 | 9/1999 |
| WO | 9945004 | 9/1999 |
| WO | 0050037 | 8/2000 |

*Primary Examiner*—Jane Fan
(74) *Attorney, Agent, or Firm*—White & Case LLP

(57) ABSTRACT

The present invention relates to novel compounds of Formula I, and pharmaceutically acceptable salts thereof, as antibacterial agents. The compounds of the present invention are nitric oxide releasing derivatives of proton pump inhibitors (NO-releasing PPIs). In further aspects, the invention relates to compounds of the invention for use in therapy; to processes for preparation of such new compounds; to pharmaceutical compositions containing at least one compound of the invention, or a pharmaceutically acceptable salt thereof, as active ingredient; and to the use of the active compounds in the manufacture of medicaments for the medical use indicated above. The invention also relates to new intermediates for use in the preparation of the novel compounds. Additionally the present invention relates to co-administration of NO-releasing PPIs with other known medicaments.

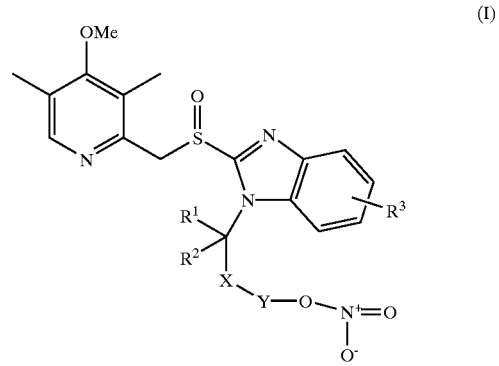

7 Claims, No Drawings

COMPOUNDS USEFUL AS ANTIBACTERIAL AGENTS

This application is a continuation-in-part of PCT/SE01/01421, filed Jun. 20, 2001, which claims priority to SE 0002476-0, filed Jun. 30, 2000. International application no. PCT/SE01/01421 published under PCT article 21(2) in English as WO 02/00166 on Jan. 3, 2002.

TECHNICAL FIELD

The present invention relates to novel compounds, and pharmaceutically acceptable salts thereof, useful as antibacterial agents. The compounds of the present invention are nitric oxide releasing derivatives of proton pump inhibitors (NO-releasing PPIs). In further aspects, the invention relates to compounds of the invention for use in therapy; to processes for preparation of such new compounds; to pharmaceutical compositions containing at least one compound of the invention, as active ingredient; and to the use of the active compounds in the manufacture of medicaments for the medical use as an antibacterial agent. The invention also relates to new intermediates for the preparation of the novel compounds. Additionally, the present invention relates to co-administration of NO-releasing PPIs with other known medicaments.

BACKGROUND ART

The compound 5-methoxy-2-[[(4-methoxy-3,5-dimethyl-2-pyridinyl)methyl]sulfinyl]-1H-benzimidazole, having the generic name omeprazole, as well as pharmaceutically acceptable salts thereof, are described in EP 5129. Omeprazole is the first member in a family called proton pump inhibitors. Proton pump inhibitors are effective in inhibiting gastric acid secretion, and are consequently useful as anti-ulcer agents and have revolutionized the treatment of gastrointestinal disorders. Omeprazole is also known from EP 414 847 to have an antibacterial effect.

Other proton pump inhibitors, such as pantoprazole, lanzoprazole, rabeprazole and leminoprazole, are all substituted benzimidazoles and therefore structurally closely related to omeprazole. Unfortunately, omeprazole and other structurally related benzimidazoles suffer from chemical instability, especially in acidic and neutral media. This makes omeprazole and other structurally related benzimidazoles difficult to handle, store and formulate.

Nitric oxide (NO) is a molecule of versatility and importance in many guises. In the atmosphere it is a noxious chemical, but in the body in small and controlled doses it is extraordinary beneficial. It helps maintain blood pressure by dilating blood vessels, helps kill foreign invaders in the immune response, is a major biochemical mediator of penile erections, and is proposed to be a major biochemical component of long-term memory.

Helicobacter pylori is a gram-negative bacterium which colonises in the gastric mucosa in mammalian animals, including human beings. A number of different therapies have been proposed for the treatment of Helicobacter pylori infections, including combination therapies. The most commonly used combination therapy comprises a proton pump inhibitor in combination with one or more antibacterial compounds, such as claritromycin and/or amoxicillin, see WO93/21920.

In view of the vast number of human beings suffering from gastrointestinal disorders caused or mediated by bacterial infections and also in view of the fact that many bacterial strains develop a resistance to commonly used antibiotics, a continuing need exists for a safe and effective medicament having an antibacterial effect, especially for the treatment of Helicobacter pylori infections.

SUMMARY OF THE INVENTION

It has surprisingly been found that compounds of the Formula I below, are particularly effective as antibacterial agents. The compounds of the invention are especially suitable for treatment of infections caused by Helicobacter pylori.

The compounds of the present invention are characterized as being NO-releasing proton pump inhibitor derivatives (NO-releasing PPI or NO-PPI). A NO-releasing proton pump inhibitor is a compound which upon administration to a mammal, e.g. a human being, generates nitric oxide and a proton pump inhibitor.

One object of the present invention is to provide novel compounds that are effective as antibacterial agents.

In one aspect, the present invention thus relates to compounds of the Formula I:

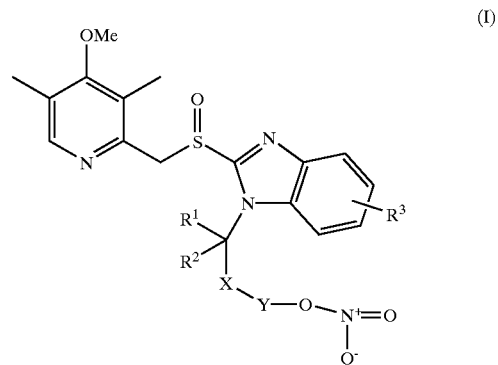

wherein,

R$^1$ is hydrogen or C$_1$–C$_6$ alkyl,

R$^2$ is hydrogen or C$_1$–C$_6$ alkyl,

R$^3$ is methoxy linked to the carbon atom in position 5 or linked to the carbon atom in position 6 of the benzimidazole moiety,

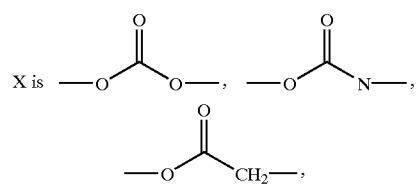

or a single bond,

Y is —(CH$_2$)$_n$—, —(CH$_2$)$_m$—O—(CH$_2$)$_p$—, or a single bond, and m, n, and p are integers and independently selected from 1 to 10, or a pharmaceutically acceptable salt or enantiomer thereof.

In accordance with one embodiment of the invention, compounds of the present invention include those compounds of formula I wherein R$^1$ and R$^2$ are hydrogen, R$^3$ is methoxy linked to the carbon atom in position 5 or linked to the carbon atom in position 6 of the benzimidazole moiety, X is 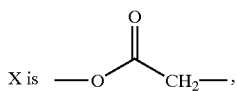

or a single bond,

Y is —(CH$_2$)$_n$—, or a single bond, and n is an integer from 1 to 10.

In accordance with another embodiment of the invention, compounds of the present invention include 1-nitrooxymethyl-(5-methoxy) 2-[[(4-methoxy-3,5-dimethyl-2-pyridyl)methyl]sulfinyl]-1H-benzimidazole and 1-nitrooxymethyl-(6-methoxy)-2-[[(4-methoxy-3,5-dimethyl-2-pyridyl)methyl]sulfinyl]-1H-benzimidazole.

Furthermore any pure enantiomer, mixture of enantiomers, and pharmaceutically acceptable salt of the compounds of the invention are within the scope of the present invention.

As used herein, the term "C$_1$–C$_6$ alkyl" denotes a straight or branched alkyl group having from 1 to 6 carbon atoms. Examples of said C$_1$–C$_6$ alkyl includes, but is not limited to, methyl, ethyl, n-propyl, iso-propyl, n-butyl, iso-butyl, sec-butyl, t-butyl and straight- and branched-chain pentyl and hexyl.

It should be clear for a person skilled in the art, that compounds of formula I is wherein X and Y may each and independently be "a single bond" means that X and Y may each and independently be directly linked to oxygen in ONO$_2$.

Preparation

The present invention also provides the following processes A and B for the manufacture of compounds of the Formula I.

Process A a) Compounds of Formula II

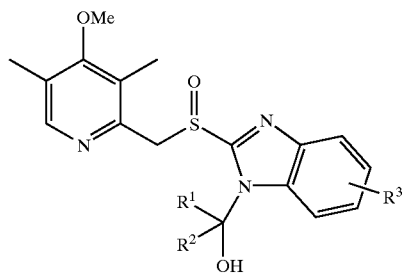

(II)

wherein R$^1$ is hydrogen or C$_1$–C$_6$ alkyl,
R$^2$ is hydrogen or C$_1$–C$_6$ alkyl, and
R$^3$ is methoxy linked to the carbon atom in position 5 or linked to the carbon atom in position 6 of the benzimidazole moiety, is reacted with thionyl chloride, or any other similar reagent, in dichloromethane, or any other similar solvent, under standard conditions to give a compound of formula III

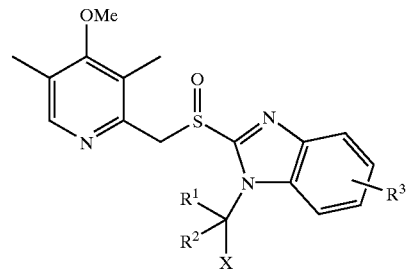

(III)

wherein R$^1$ is hydrogen or C$_1$–C$_6$ alkyl,
R$^2$ is hydrogen or C$_1$–C$_6$ alkyl,
R$^3$ is methoxy linked to the carbon atom in position 5 or linked to the carbon atom in position 6 of the benzimidazole moiety, and
X$^1$ is halogen, such as chloride.

b) Compounds of Formula III is thereafter reacted with silver nitrate in a suitable solvent, such as acetonitrile under standard conditions to give compounds of Formula I wherein
R$^1$ is hydrogen or C$_1$–C$_6$ alkyl,
R$^2$ is hydrogen or C$_1$–C$_6$ alkyl,
R$^3$ is methoxy linked to the carbon atom in position 5 or linked to the carbon atom in position 6 of the benzimidazole moiety, and
X and Y are a single bonds Process B a) Compounds of Formula II

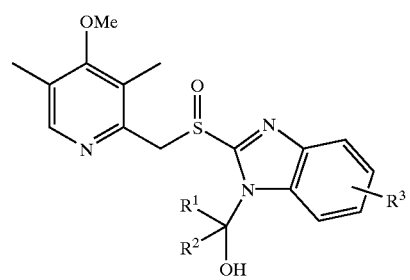

(II)

wherein R$^1$ is hydrogen or C$_1$–C$_6$ alkyl,
R$^2$ is hydrogen or C$_1$–C$_6$ alkyl,
R$^3$ is methoxy linked to the carbon atom in position 5 or linked to the carbon atom in position 6 of the benzimidazole moiety, and is reacted with a compound of the formula IV

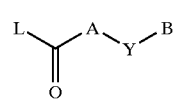

(IV)

wherein L is —Br or —Cl,
A is —N—, —O—, or —CH$_2$—,
B is —Br or —Cl,
Y is —(CH$_2$)$_n$—, or —(CH$_2$)$_m$—O—(CH$_2$)$_p$—, or a single bond;
m, n, and p are integers and independently selected from 1 to 10, under standard conditions to give a compound of Formula V

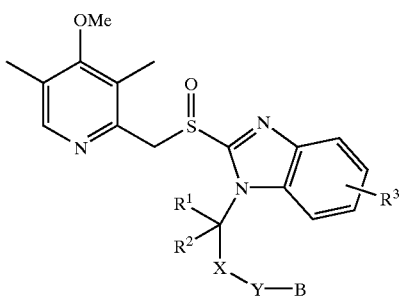

(V)

wherein
- $R^1$ is hydrogen or $C_1$–$C_6$ alkyl,
- $R^2$ is hydrogen or $C_1$–$C_6$ alkyl,
- $R^3$ is methoxy linked to the carbon atom in position 5 or linked to the carbon atom in position 6 of the benzimidazole moiety,
- B is —Br or —Cl,

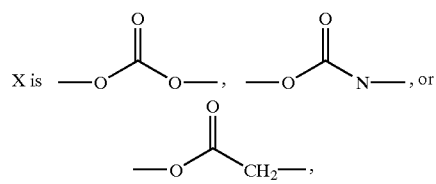

Y is —$(CH_2)_n$—, —$(CH_2)_m$—O—$(CH_2)_p$—, or a single bond, and m, n, and p are integers and independently selected from 1 to 10.

b) Compounds of Formula V is thereafter reacted with silver nitrate in a suitable solvent, such as acetonitrile under standard conditions to give compounds of Formula I wherein
- $R^1$ is hydrogen or $C_1$–$C_6$ alkyl,
- $R^2$ is hydrogen or $C_1$–$C_6$ alkyl,

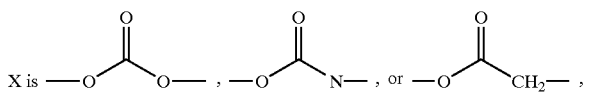

Y is —$(CH_2)_n$—, —$(CH_2)_m$—O—$(CH_2)_p$—, or a single bond, and m, n, and p are integers and independently selected from 1 to 10.

Compounds of Formula II may be prepared according to the procedure disclosed in WO87/02668.

Medical Use

In a further aspect, the invention relates to compounds of formula I for use in therapy, in particular for use as an antibacterial agent. The invention also provides the use of a compound of formula I in the manufacture of a medicament for use as an antibacterial agent.

The typical daily dose of the active substance varies within a wide range and will depend on various factors such as e.g. the individual requirement of each patient and the route of administration. In general, oral and parenteral dosages will be in the range of 5 to 1000 mg per day of active substance.

Pharmaceutical Formulations

In yet a further aspect, the invention relates to pharmaceutical compositions containing at least one compound of the invention, or a pharmaceutically acceptable salt thereof, as active ingredient.

For clinical use, the compounds of the invention are formulated into pharmaceutical formulations for oral, rectal, parenteral or any other mode of administration. The pharmaceutical formulation contains at least one compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.1–20% by weight in preparations for parenteral use and preferably between 0.1 and 50% by weight in preparations for oral administration.

In the preparation of pharmaceutical formulations containing at least one compound of the present invention in the form of dosage units for oral administration the compound selected may be mixed with solid, powdered ingredients, or another suitable ingredient, as well as with disintegrating agents and lubricating agents. The mixture is then processed into granules or pressed into tablets.

Soft gelatin capsules may be prepared with capsules containing a mixture of the active compound or compounds of the invention. Hard gelatin capsules may contain granules of the active compound. Hard gelatin capsules may also contain the active compound in combination with solid powdered ingredients.

Dosage units for rectal administration may be prepared (i) in the form of suppositories which contain the active substance mixed with a neutral fat base; (ii) in the form of a gelatin rectal capsule which contains the active substance in a mixture with suitable vehicles for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the active ingredient. If desired, such liquid preparations may contain coloring agents, flavoring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of at least one compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to by reconstituted with a suitable solvent extemporaneously before use.

Combination Therapy

The compounds according to the present invention, or any other NO-releasing PPI, can also be used in formulations, together or in combination for simultaneous, separate or sequential use, with other active ingredients, e.g. for the treatment or prophylaxis of conditions involving infection by *Helicobacter pylori*. Such other active ingredients may be other antibacterial agents, in particular:

β-lactam antibiotics such as amoxicillin, ampicillin, cephalothin, cefaclor or cefixime;

macrolides such as erythromycin, or clarithromycin;
tetracyclines such as tetracycline or doxycycline;
aminoglycosides such as gentamycin, kanamycin or amikacin;
quinolones such as norfloxacin, ciprofloxacin or enoxacin;
others such as metronidazole, nitrofurantoin or chloramphenicol; or
preparations containing bismuth salts such as bismuth subcitrate, bismuth subsalicylate, bismuth subcarbonate, bismuth subnitrate or bismuth subgallate; or NSAID (non-steroidal antiinflammatory drugs) in particular:
ibuprofen, indomethacin, diclofenac, ketorolac, naproxen, ketoprofen, mefenamic acid, flunixin, flufenamic acid, or niflumic acid.

The compounds according to the present invention, or any other NO-releasing PPI, can also be used together or in combination for simultaneous, separate or sequential use in therapy, e.g. for the treatment or prophylaxis of gastrointestinal disorders, with the following medicaments:
antacids such as aluminium hydroxide, magnesium carbonate and magnesium hydroxid or alginic acid;
H2-blockers (e.g cimetidine, ranitidine);
gastroprokinetics (e.g. cisapride or mosapride); or
other antibacterial agents and NSAIDs, in particular those indicated above.

In one aspect of the present invention, the pharmaceutical combinations of the invention may be administered as a pharmaceutical formulation, which in addition to the active compounds further may include a pharmaceutically acceptable carrier or adjuvant. In a further aspect of the invention, each active compound may be administered for combination therapy by simultaneous, or separate administration in a sequential order, i.e. one after the other. Thus, a further aspect of the invention is a kit comprising an NO-releasing PPI in combination with any one of the drugs mentioned above, suitable for combination therapy.

Intermediates

A further aspect of the invention is novel intermediate compounds, which are useful in the preparation of compounds according to the present invention.

Thus, one object of the invention is a compound of the formula III

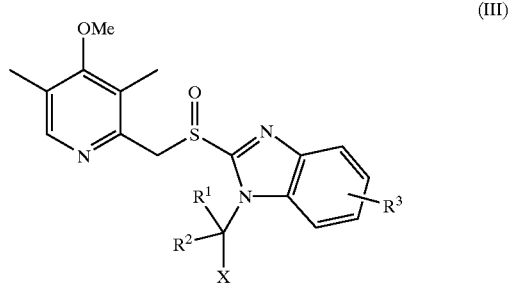

(III)

wherein R$^1$ is hydrogen or C$_1$–C$_6$ alkyl,
R$^2$ is hydrogen or C$_1$–C$_6$ alkyl,
R$^3$ is methoxy linked to the carbon atom in position 5 or linked to the carbon atom in position 6 of the benzimidazole moiety, and
X$^1$ is halogen, such as chloride,
or any enantiomer or salt thereof.

Another object of the invention is a compound of the Formula V

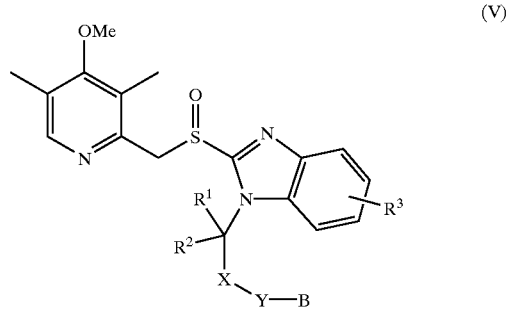

(V)

wherein
R$^1$ is hydrogen or C$_1$–C$_6$ alkyl,
R$^2$ is hydrogen or C$_1$–C$_6$ alkyl,
R$^3$ is methoxy linked to the carbon atom in position 5 or linked to the carbon atom in position 6 of the benzimidazole moiety,
B is —Br or —Cl,

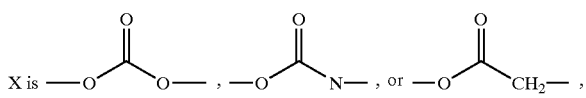

Y is —(CH$_2$)$_n$—, —(CH$_2$)$_m$—O—(CH$_2$)$_p$—, or a single bond, and
m, n, and p are integers and independently selected from 1 to 10, or any enantiomer or salt thereof.

EXAMPLES

Example 1.1

Synthesis of 1-Chloromethyl-(5-methoxy) and 1-chloromethyl-(6-methoxy)-2-[[(4-methoxy-3,5-dimethyl-2-pyridyl)methyl]sulfinyl]-1H-benzimidazole (isomermixture 1:2)

1-Hydroxymethyl-(5-methoxy) and 1-hydroxymethyl-(6-methoxy)-2-[[(4-methoxy-3,5-dimethyl-2-pyridyl)methyl]sulfinyl]-1H-benzimidazole (isomer mixture 1:2) (2.3 g, 6 mmol) and triethyl amine (0.9 g, 8.8 mmol) were dissolved in dichloromethane (100 ml). A solution of thionyl chloride (1.2 g, 8 mmol) in dichloromethane (10 ml) was added with such a velocity that the reaction mixture refluxed gently. After 10 minutes at ambient temperature the dichloromethane was distilled off at reduced pressure and the residue was partitioned between ethyl acetate (100 ml) and water (50 ml). When separated, the organic phase was dried over sodium sulphate, filtered and concentrated at reduced pressure. The residue was chromatographed on SiO$_2$ (ethyl acetate) and the title compound was isolated as an oil. Yield: 470 mg (1.26 mmol) 21%.

1H-NMR (400 MHz, CDCl$_3$, δ): 2.23, 2.25, 2.26, 3.72, 3.85, 3.87, 4.86, 4.89, 4.90, 4.94, 4.95, 4.98, 6.16, 6.17, 6.19, 6.20, 6.52, 6.55, 6.58, 6.95, 7.01, 7.42, 7.68, 8.18.

Mass (electrospray) (M+1): 394

Example 1.2

Synthesis of 1-Nitrooxymethyl-(5-methoxy) and 1-nitrooxymethyl-(6-methoxy)-2-[[(4-methoxy-3,5-dimethyl-2-pyridyl)methyl]sulphinyl]-1H-benzimidazole (isomermixture 1:3)

1-Chloromethyl-(5-methoxy) and 1-chloromethyl-(6-methoxy)-2-[[(4-methoxy-3,5-dimethyl-2-pyridyl)methyl]

sulphinyl]-1H-benzimidazole (isomer mixture 1:2) (470 mg, 1.26 mmol) was dissolved in acetonitrile (50 ml). Silver nitrate (240 mg, 1.4 mmol) was added and the mixture was stirred at ambient temperature for 2 h, whereupon the solvent was distilled off at reduced pressure. The residue was partitioned between ethyl acetate (50 ml) and water (50 ml). When separated, the organic phase was dried over sodium sulphate, filtered and concentrated at reduced pressure. The residue was chromatographed on $SiO_2$ (ethyl acetate/acetone 2:1) and the title compound was isolated as a solid. Yield: 95 mg (0.22 mmol) 18%.

1H-NMR (400 MHz, CDCl3, δ): 2.21, 2.26, 3.72, 3.86, 3.90, 4.88, 4.93, 4.94, 4.99, 6.72, 6.76, 6.80, 6.84, 7.02, 7.07, 7.10, 7.25, 7.45, 7.48, 7.66, 7.69, 8.12.

Mass (electrospray) (M+1): 421

Example 2.1

Synthesis of (S)1-Hydroxymethyl-(5-methoxy)- and (S)1-hydroxymethyl-(6-methoxy)-2-[[(4-methoxy-3, 5-dimethyl-2-pyridyl)methyl]sulfinyl]-1H-benzimidazole (isomer mixture 1:2)

(S)5-Methoxy-2-[[(4-methoxy-3,5-dimethyl-2-pyridyl) methyl]sulfinyl]-1H-benzimidazole (3.5 g; 10 mmol) and triethyl amine (100 mg; 1 mmol) were dissolved in methylene chloride (50 ml). A formaldehyde solution (5 M;10 ml; 50 mmol) was added and the mixture was shaken violently for 2 minutes. After separation the organic was dried over sodium sulphate, filtered and concentrated at reduced pressure. The slightly red residue (ca 4 g) was an isomeric mixture (ratio 1:2) of the title compounds. This oil was used without purification in the subsequent reactions.

$^1$H-NMR (500 MHz, CDCl$_3$, δ): 7.97, 7.93, 7.56, 7.44, 7.15, 7.05, 6.99, 6.95, 6.11, 5.68, 4.89, 3.89, 3.73, 2.32, 2.30, 2.17, 2.15.

Example 2.2

Synthesis of (S)1-Chloromethyl-(5-methoxy) and (S)1-chloromethyl-(6-methoxy)-2-[[(4-methoxy-3,5-dimethyl-2-pyridyl)methyl]sulfinyl]-1H-benzimidazole (isomer mixture 1:2)

(S)1-Hydroxymethyl-(5-methoxy) and (S)1-hydroxymethyl-(6-methoxy)-2-[[(4-methoxy-3,5-dimethyl-2-pyridyl)methyl]sulfinyl]-1H-benzimidazole (isomer mixture 1:2) (4 g, ca 10 mmol) and triethyl amine (3.3 g, 30 mmol) were dissolved in methylene chloride (100 ml) and cooled in an ice bath. A solution of thionyl chloride (1.2 g, 10 mmol) in methylene chloride (10 ml) was added with such a velocity (ca 2 min) that the temperature of the reaction mixture didn't rise above 10° C. After 10 minutes in the ice bath the methylene chloride was distilled off at reduced pressure and the residue was partitioned between ethyl acetate (100 ml) and water (50 ml). When separated, the organic phase was dried over sodium sulphate, filtered and concentrated at reduced pressure. The residue was chromatographed on $SiO_2$ (ethyl acetate) and the title compound was isolated as an oil. Yield: 1.2 g (3 mmol) (30%).

$^1$H-NMR (600 MHz, CDCl$_3$, δ): 8.18, 7.68, 7.43, 7.11, 7.01, 6.56, 6.53, 6.17, 4.97, 4.87, 3.92, 3.86, 3.72, 2.25, 2.23.

Mass (electrospray) (M+1): 394

Example 2.3

Synthesis of (S)1-Nitrooxymethyl-(5-methoxy) and (S)1-nitrooxymethyl-(6-methoxy)-2-[[(4-methoxy-3, 5-dimethyl-2-pyridyl)methyl]sulfinyl]-1H-benzimidazole (isomer mixture 1:2)

(S)1-Chloromethyl-(5-methoxy) and (S)1-chloromethyl-(6-methoxy)-2-[[(4-methoxy-3,5-dimethyl-2-pyridyl) methyl]sulfinyl]-1H-benzimidazole (isomer mixture 1:2) (0.6 g, 1.52 mmol) was dissolved in acetonitrile (50 ml). Silver nitrate (0.3 g, 1.8 mmol) was added and the mixture was stirred at ambient temperature for 2 h, whereupon the solvent was distilled off at reduced pressure. The residue was partitioned between ethyl acetate (50 ml) and water (50 ml). When separated, the organic phase was dried over sodium sulphate, filtered and concentrated at reduced pressure. The residue was chromatographed on a reversed phase column (C8; acetonitrile/water 50:50; buffer 0.1 M ammonium acetate). After freeze drying the title compound was isolated as a solid. Yield: 0.13 mg (0.31 mmol) (20%).

$^1$H-NMR (600 MHz, CDCl$_3$, δ): 8.10, 7.65, 7.45, 7.07, 7.01, 6.99, 6.79, 6.73, 4.91, 3.89, 3.84, 3.71, 2.25, 2.20.

Mass (electrospray) (M+1): 421.

Example 3.1

Synthesis of (S)(5-Methoxy- and 6-methoxy-2-{[(4-methoxy-3,5-dimethylpyridin-2-yl)methyl]sulfinyl}-1H-benzimidazol-1-yl)methyl-4-nitrooxybutanoate (isomer mixture 1:2)

(S)1-Hydroxymethyl-(5-methoxy)- and (S)1-hydroxymethyl-(6-methoxy)-2-[[(4-methoxy-3,5-dimethyl-2-pyridyl)methyl]sulfinyl]-1H-benzimidazole (isomer mixture 1:2) (4 g, ca 10 mmol) and triethyl amine (3.3 g, 30 mmol) were dissolved in methylene chloride (100 ml) and cooled in an ice bath. 4-Nitrooxybutanoyl chloride (2.5 g; 15 mmol) was added and after 10 min at ambient temperature the solvent was distilled off at reduced pressure. The residue was partitioned between ethyl acetate (50 ml) and water (50 ml). After separation, the organic phase was dried over sodium sulphate, filtered and concentrated at reduced pressure. The residue was chromatographed on $SiO_2$ (ethyl acetate). The title compound was isolated as a solid. Yield: 3.5 g (6.9 mmol) (69%).

$^1$H-NMR (600 MHz, CDCl$_3$, δ): 8.09, 7.65, 7.46, 7.22, 7.08, 7.02, 6.97, 6.42, 4.92, 4.45, 3.88, 3.84, 3.70, 3.49, 2.27, 2.19, 2.04.

Mass (electrospray) (M+1): 507.

Biological Tests

Strain: *Helicobacter pylori* reference strain NCTC 11 637 (National Type Culture Collection, from Smittskyddsinstitutet in Solna, Sweden), an antibiotic sensitive reference strain Substance: as prepared in Example 1.2

*Helicobacter pylori* was grown on blood agar plates, having a diameter of 90 mm, for three days under microaerophilic conditions at 37° C. The bacteria were suspended in PBS (phosphate buffer saline) to approximately $10^8$ cfu/ml. Approximately 2 ml of the suspension was added to one agar plate and spread even on the surface of the agar. Overflow was removed with a syringe. Wells, like small holes, 3 mm in diameter, were made in the agarplate by removing agar. Three wells per plate were made. A stock solution of a compound of the present invention having the concentration 100 000 μg/ml was prepared. 30 μl of the solution was added to the wells. The plates were incubated for four days before they were checked for inhibition zones around the wells.

What is claimed is:

1. An isomer mixture consisting of a 5-methoxy isomer and a 6-methoxy isomer of a compound of formula I or a pharmaceutically acceptable salt or enantiomer thereof

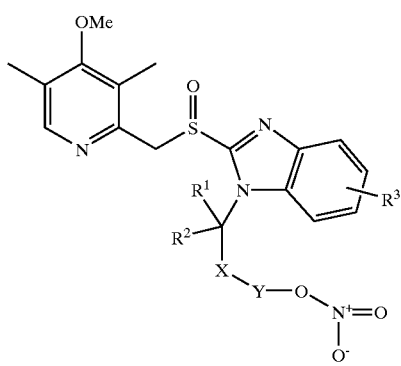

(I)

wherein,

R¹ is hydrogen or $C_1$-$C_6$ alkyl,

R² is hydrogen or $C_1$-$C_6$ alkyl,

R³ is methoxy linked to the carbon atom in position 5 or linked to the carbon atom in position 6 of the benzimidazole moiety,

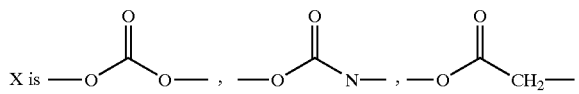

or a single bond

Y is —(CH$_2$)$_n$—, —(CH$_2$)$_m$—O—(CH$_2$)$_p$—, or a single bond, and m, n, and p are integers and independently selected from 1 to 10.

2. The isomer mixture according to claim 1, wherein, in the compound of formula I:

R¹ and R² are hydrogen,

R³ is methoxy linked to the carbon atom in position 5 or linked to the carbon atom in position 6 of the benzimidazole moiety,

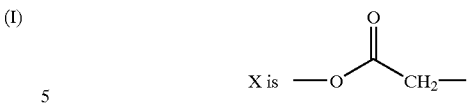

or a single bond,

Y is —(CH$_2$)$_n$—, or a single bond, and n is an integer from 1 to 10.

3. The isomer mixture according to claim 1, wherein the 5-methoxy isomer is 1-nitrooxymethyl-(5-methoxy)-2-[[(4-methoxy-3,5-dimethyl-2-pyridyl)methyl]sulfinyl]-1H-benzimidazole or 1-nitrooxymethyl-(6-methoxy)-2-[[(4-methoxy-3,5-dimethyl-2-pyridyl)methyl]sulfinyl]-1H-benzimidazole and the 6-methoxy isomer is 1-nitrooxymethyl(6-methoxy)-2[[(4-methoxy-3,5-dimethyl-2-pyridyl)methyl]sulfinyl]-1H-benzimidazole.

4. A pharmaceutical formulation comprising the isomer mixture according to any one of claims 1–3, 6 or 7 as active ingredient in combination with a pharmaceutically acceptable diluent or carrier.

5. A method for the treatment or prophylaxis of conditions involving infection by *Helicobacter pylori*, which comprises administering to a mammal in need of such treatment an effective amount of the isomer mixture according to any one of claims 1–3, 6 or 7.

6. The isomer mixture according to claim 1, wherein the 5-methoxy isomer is (S)(5-methoxy-2-
-1H benzimidazol-1-yl)methyl4-nitrooxybutanoate and the 6-methoxy isomer is (S)(6-methoxy-2-
-1H-benzimidazol-1yl)methyl4-nitrooxybutanoate.

7. The isomer mixture according to claim 1, wherein the 5-methoxy isomer is (S)1-nitrooxymethyl-(5-methoxy)-2-[[(4-methoxy-3,5-dimethyl-2-pyridyl)methyl]sulfinyl]-1H-benzimidazole and the 6-methoxy isomer is (S)1-nitrooxymethyl-(6-methoxy)-2-[[(4-methoxy-3,5-dimethyl-2-pyridyl)methyl]sulfinyl]-1H-benzimidazole.

* * * * *

UNITED STATES PATENT AND TRADEMARK OFFICE
CERTIFICATE OF CORRECTION

PATENT NO.    : 6,673,819 B2
DATED         : January 6, 2004
INVENTOR(S)   : Bergman et al.

It is certified that error appears in the above-identified patent and that said Letters Patent is hereby corrected as shown below:

Column 12,
Lines 11-18, should read as follows:
3. The isomer mixture according to claim 1, wherein the 5-methoxy isomer is 1-nitrooxymethyl-(5-methoxy)-2-[[(4-methoxy-3,5-dimethyl-2-pyridyl)methyl]sulfinyl]-1H-benzimidazole and the 6-methoxy isomer is 1 nitrooxymethyl-(6-methoxy)-2-[[(4-methoxy-3,5-dimethyl-2-pyridyl)methyl]sulfinyl]-1H-benzimidazole.
Lines 28-33, should read as follows:
6. The isomer mixture according to claim 1, wherein the 5-methoxy isomer is (S)(5-methoxy-2-{[(4-methoxy-3,5-dimethylpyridin-2-yl)methyl]sulfinyl}-1H-benzimidazol-1-yl)methyl4-nitrooxybutanoate and the 6 methoxy isomer is (S)(6-methoxy-2-{[(4-methoxy-3,5-dimethylpyridin-2-yl)methyl]sulfinyl}-1H-benzimidazol-1-yl)methyl4-nitrooxybutanoate.

Signed and Sealed this

Twenty-third Day of March, 2004

JON W. DUDAS
*Acting Director of the United States Patent and Trademark Office*